United States Patent
Secq

(10) Patent No.: US 7,520,177 B2
(45) Date of Patent: Apr. 21, 2009

(54) COLLAR FOR MEASURING THE LATERAL DEFORMATION OF A TEST PIECE DURING COMPRESSION TEST, SUCH AS UNIAXIAL OR TRIAXIAL COMPRESSION TESTS

(75) Inventor: Jean Secq, Villeneuve d'Asq (FR)

(73) Assignee: Universite des Sciences et Technologies de Lille, Villeneuve d'Asq (FR)

( * ) Notice: Subject to any disclaimer, the term of this patent is extended or adjusted under 35 U.S.C. 154(b) by 0 days.

(21) Appl. No.: 11/914,227

(22) PCT Filed: May 22, 2006

(86) PCT No.: PCT/FR2006/001165

§ 371 (c)(1),
(2), (4) Date: Nov. 12, 2007

(87) PCT Pub. No.: WO2006/125904

PCT Pub. Date: Nov. 30, 2006

(65) Prior Publication Data

US 2008/0190211 A1 Aug. 14, 2008

(30) Foreign Application Priority Data

May 24, 2005 (FR) ................................. 05 05203

(51) Int. Cl.
*G01N 3/00* (2006.01)
*G01N 33/24* (2006.01)
*G01N 33/38* (2006.01)

(52) U.S. Cl. ......................................... 73/795; 73/866

(58) Field of Classification Search ................... 73/794, 73/795, 866
See application file for complete search history.

(56) References Cited

U.S. PATENT DOCUMENTS

| 3,779,085 A | * | 12/1973 | Rice .............................. 73/866 |
| 4,579,003 A | | 4/1986 | Riley et al. |
| 4,587,739 A | * | 5/1986 | Holcomb et al. .............. 33/783 |
| 4,905,521 A | | 3/1990 | Wagner et al. |
| 5,123,283 A | * | 6/1992 | Duff et al. ...................... 73/760 |
| 5,275,063 A | * | 1/1994 | Steiger et al. .............. 73/865.6 |
| 5,483,836 A | | 1/1996 | Kennebrew et al. |
| 2005/0039540 A1 | * | 2/2005 | Crockford .................... 73/784 |

FOREIGN PATENT DOCUMENTS

FR 2566531 12/1985
FR 2663121 12/1991

* cited by examiner

*Primary Examiner*—Lisa M Caputo
*Assistant Examiner*—Punam Patel
(74) *Attorney, Agent, or Firm*—Egbert Law Offices PLLC

(57) ABSTRACT

The invention relates to a collar for measuring lateral deformation of a test piece during uniaxial or triaxial compression tests. According to the invention, the collar includes a metal hoop or a hoop that is made from composite materials, which can clasp the test piece. When the hoop is open, the free ends thereof are separated by a distance Δ. The inventive collar is also equipped with a measurement device for directly or indirectly measuring the distance Δ. Between the free ends of the hoop, the device can be a linear variable differential transformer-type probe. The invention also relates to a protective sleeve for the test piece, which can co-operate with the collar.

9 Claims, 3 Drawing Sheets

COLLAR FOR MEASURING THE LATERAL DEFORMATION OF A TEST PIECE DURING COMPRESSION TEST, SUCH AS UNIAXIAL OR TRIAXIAL COMPRESSION TESTS

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The invention concerns a collar for measuring the lateral deformation of a test piece during compression tests, in particular uniaxial or triaxial. It will find a particular application in a polyvalent triaxial test cell for rock sample geomaterials, such as soil, concrete and cimentitious materials or fabricated materials, on the sampling sites, in laboratory test conditions.

2. Description of Related Art Including Information Disclosed Under 37 CFR 1.97 and 37 CFR 1.98.

Such samples, also called test pieces, cylindrical in shape, may be subjected to different pressure conditions, load, temperature, and drainage conditions, wherein said parameters may be controlled using pressure, temperature, internal or external displacement sensors. The pressure stresses may be directed axially and/or to the lateral face of the sample.

Document FR-2.566.531 divulges a lateral displacement sensor, in the form of a collar, formed by a plurality of parallel rolls, hinged together, and capable of clamping the sample held by a spring-loaded system. Such collar enables measurement of the lateral deformation of the sample while measuring the spacing of both last rolls.

Document FR-2.663.121 divulges a polyvalent triaxial test cell for geomaterials. Such a cell includes a pressure chamber inside which is placed the cylindrical test piece. It includes at least one compression jack capable of exerting uniaxial thrust longitudinally to the test piece.

A lateral pressure, and more particularly radial, is exerted on the test piece while subjecting the lateral face of said cylindrical test piece to the pressure of a fluid. A hydraulic compensation system enables moreover to balance the longitudinal and radial loads.

Also, the sample is immersed in a fluid, such as oil, and is protected from said fluid by means of a sheath in the form of a sleeve formed of an elastic diaphragm. In order to measure the lateral deformation of the sample, a collar of known type, formed of rolls, is placed around the sheath while hugging it.

Nevertheless, such a collar proves little satisfactory, since these rolls have a tendency to impress in the elastic wall of the diaphragm, thereby disturbing their displacement by rolling around the periphery of the sleeve.

Moreover, it has been noticed that the elasticity of the wall of the diaphragm twists the measurement, wherein the collar measures the lateral deformation of the sample, but also the lateral deformation of said diaphragm.

Moreover, the collar known aforementioned, formed of rolls, proves relatively cumbersome and requires a test cell whereof the pressure chamber is sufficiently large, in particular in width, to be installable.

BRIEF SUMMARY OF THE INVENTION

The aim of the present invention is to provide a collar measuring the lateral deformation of a test piece which remedies the shortcomings aforementioned.

Another aim of the invention is to provide a measuring collar, simple in its design and at low cost.

Another aim of the invention is to provide a measuring collar, capable of co-operating with a standard uni-axial displacement measuring sensor.

Another aim of the invention is to provide a measuring collar enabling increase or decrease in measuring sensitivity.

Another aim of the invention is to offer a protective sheath for specific test piece, suited to be used with a collar according to the invention. Other aims and advantages of the present invention will appear from the following description, given solely by way of example and without being limited thereto.

The invention relates first of all to a collar for measuring the lateral deformation of a test piece during compression tests, in particular uniaxial or triaxial. The collar is formed of a metal ring or a ring made of composite materials, capable of clamping said test piece and being open. The free ends are spaced apart by a distance A, said collar exhibiting moreover means for measuring, directly or indirectly, the spacing A. The free ends of the ring are formed by a sensor of a linear variation differential transformer type.

The invention also relates to a sheath, intended for being used in a test cell, in order to protect a test piece, in particular a mineral, rock and/or concrete soil and cimentitious materials. The sheath is formed by an elastic sleeve and is capable of co-operating with a measuring collar, in particular, according to the invention.

BRIEF DESCRIPTION OF THE SEVERAL VIEWS OF THE DRAWINGS

According to the invention, the sleeve exhibits in its wall at least two hard spots, spread regularly on the circumference of said sleeve, capable of forming resting points for said collar.

The invention will be understood better when reading the following description accompanied by the appended drawings.

DETAILED DESCRIPTION OF THE INVENTION

Figure 1:
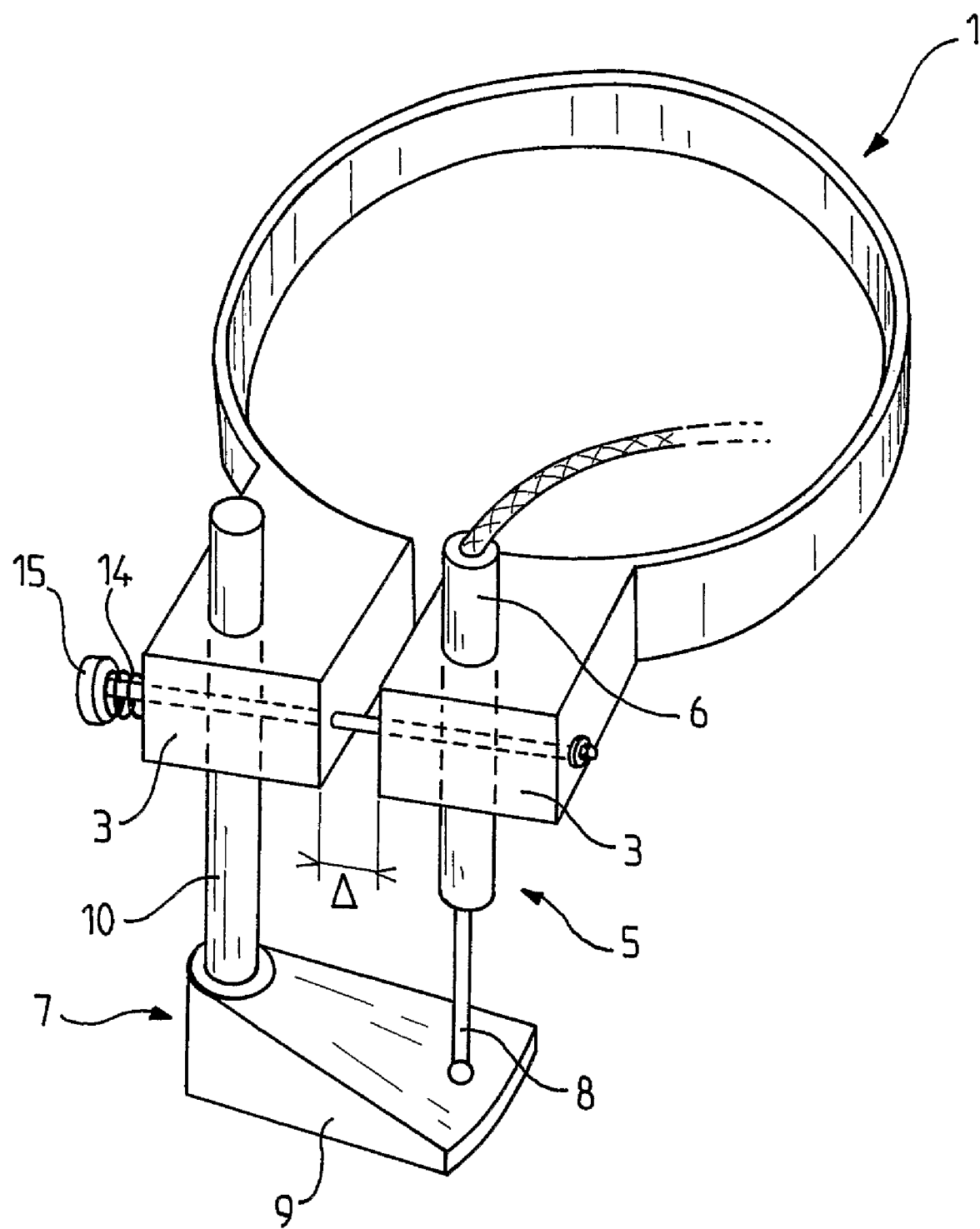
FIG. 1 is a perspective view of a collar according to the invention.

The invention relates first of all to a collar 1 for measuring the lateral deformation of a test piece during compression tests, in particular uniaxial or triaxial.

By lateral, deformation is meant a deformation of the test piece in a plane perpendicular to the longitudinal axis of the cylindrical test piece.

According to the invention, the collar 1 is formed of a metal ring 2 or a ring made of composite materials, capable of clamping said test piece. The ring is open. The metal ring or ring made of composite materials can be composed of a single-piece or two adjoining portions, for instance by welding, in particular rigid or semi-rigid. It clamps the test piece by hugging it.

The free ends 3 of the ring 2 are spaced apart by a distance A.

Said collar 1 exhibits moreover means 8, 9 for measuring, directly or indirectly, the spacing A of said free ends 3 of the ring 2. The means are formed by a sensor of linear variation differential transformer type.

The sensor of linear variation differential transformer type is also known as LVDT.

According to an embodiment, the collar exhibits moreover measurement of mechanical feedback means. Also, as illustrated on FIG. 1, the globally cylindrical body of the sensor can be slaved to one of the free ends 3, perpendicular to the plane of the collar thereby enabling reduction of the lateral space requirements of the device.

According to an embodiment, the sensor 6 is slaved to one of the free ends 3 of the ring. The finger 8 of the sensor is arranged substantially perpendicular to the plane of the ring and is capable of co-operating with a cam 9 slaved to the other free end 3 of the ring. The cam 9 is slaved to one end of a positioning rod 10 and exhibits, in particular, a cone-shaped portion, whereof the generatrix is capable of cooperating with the finger 8 of the sensor.

Figure 2:
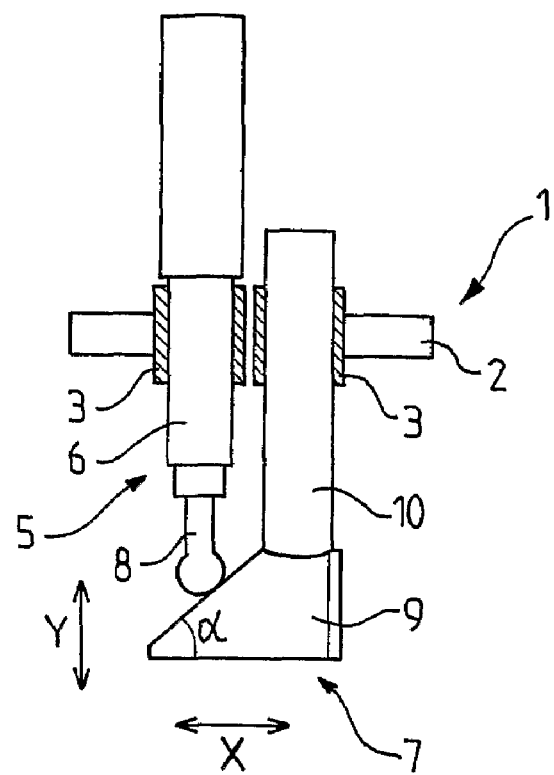
FIG. 2 is a sectional view of diagram along a vertical section of the collar as illustrated in FIG. 1.

As illustrated in FIG. 1 or 2, the longitudinal axis of the positioning rod is arranged substantially parallel to the longitudinal axis of the body of the sensor.

According to an embodiment, the cam exhibits an angle slope relative to a plane perpendicular to the longitudinal axis of the finger 8 of the sensor, enabling adjustment of the sensitivity of the measurement.

As illustrated on FIG. 2, the generatrix of the cone portion forms an angle "a" with a plane parallel to the plane of the ring. Also, for a relative displacement X between the free ends 3 of the ring 2, the finger of the sensor moves over a distance Y=tana.

The selection of the angle "a" then enables adaptation of the collar to the stroke of the sensor, let alone increase the sensitivity of the measurement. Thus, for an angle greater than 45 degrees, the cam acts as a mechanical amplifier.

Advantageously, the cam can be removable.

According to the sensor used, the usage or the desired sensitivity, it is thus possible to have a set of several cams exhibiting different degrees of angle "a".

According to an embodiment, at least one free end 3 of the ring 2 exhibits a through-bore 11 perpendicular to the plane of the ring, for fastening the cam 9 or for fastening the body of the sensor 6. Said bore exhibits an orthogonal bore 12 tapped and emerging at said through-bore, capable of cooperating with a locking screw.

Figure 3:
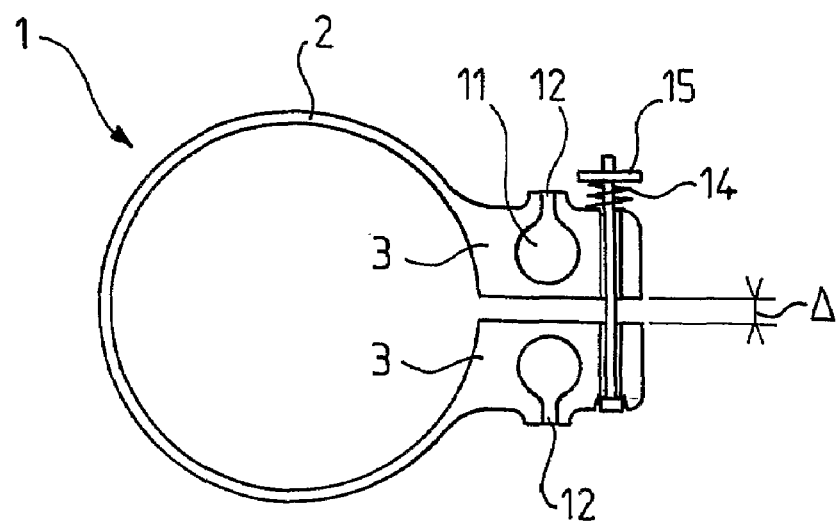
FIG. 3 is a partial, horizontal sectional view of the collar as illustrated on FIG. 1.

As illustrated on FIG. 3, the free ends 3 of the ring are each formed by a material protrusion, substantially parallel to one another. Said through-bores 11 have diameters large enough to be traversed by the body of the sensor 6 or still by the positioning rod 10 of the cam 9. The latter may be adjusted in said bores in particular by means of a non-illustrated spacer ring.

According to an embodiment, both free ends 3 of the ring are traversed by a guiding rod in particular fitted with resilient means 14. This guiding rod enables the collar to deform in a controlled fashion, in particular without any twist, so that said free ends 3 are kept substantially opposite to one another.

The resilient means 14 may be in the form of a compression spring resting on the one hand on a free end 3 of the ring 2 and on the other hand on a nut 15 screwed to one of the threaded ends of the guiding rod.

Advantageously, the nut 15 enables adjustment of the recall force of the resilient means 14.

However, the invention also relates to a sheath 20 intended for being used in a test cell, such as that for instance described in document FR-2,663.121, in order to protect a test piece 21, of a particular mineral, rock and/or soil, concrete, or cimentitious material. The sheath 20 is formed of a resilient sleeve 22 and is capable in particular of co-operating with a measuring collar according to the invention.

According to the invention, the sleeve 22 exhibits, in its wall, at least two hard spots 24, spread regularly on the circumference of said sleeve, capable of forming resting points for said collar. The sleeve can be realized from an elastic diaphragm, in particular, from an elastomer. Advantageously, the hard spots consist of elements of much higher stiffness than said elastic diaphragm, and of higher stiffness than that of the test piece. Also, during the tests, the deformation of said element forming the hard spots is negligible relative to that of the test piece. The sleeve exhibits, according to an embodiment, four points spread regularly on the circumference of said sleeve at 90°.

According to an embodiment, each hard spot 24 formed by a insert of thickness substantially equal to the thickness of the wall of the sleeve and flush with both sides of said wall. The insert exhibits moreover interlocking means 25, 26 for retaining said insert to the sleeve 22.

Figure 4:
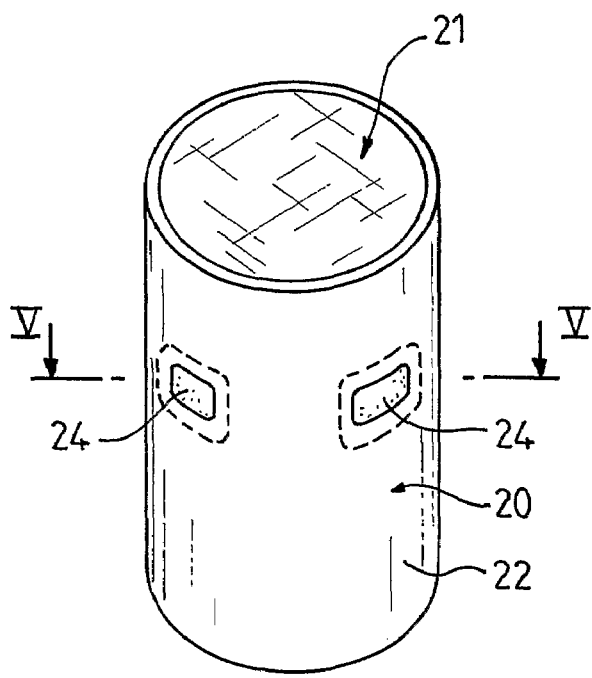
FIG. 4 is a perspective view of a test piece and a sheath according to the invention.
Figure 5:
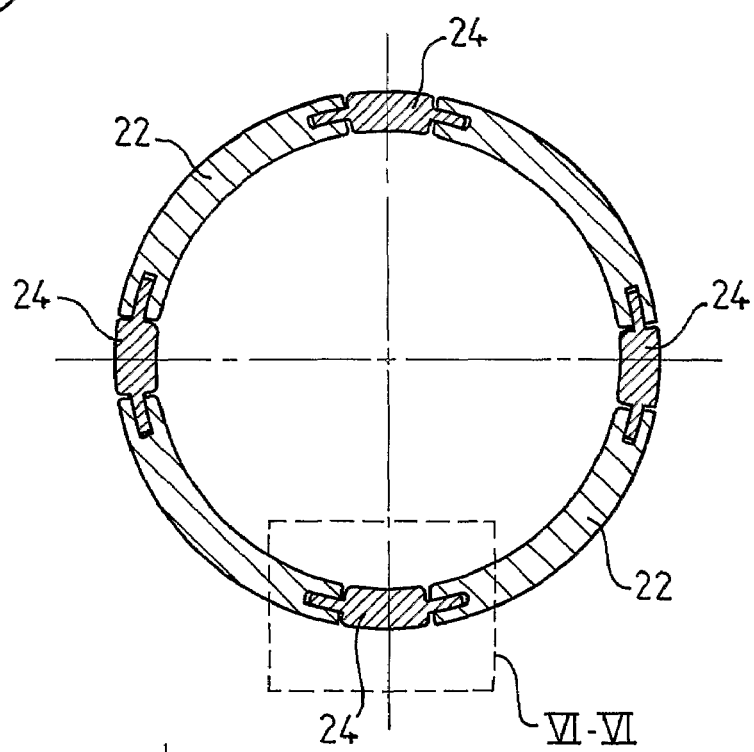
FIG. 5 is a sectional view along the horizontal section V-V as illustrated on FIG. 4.
Figure 6:
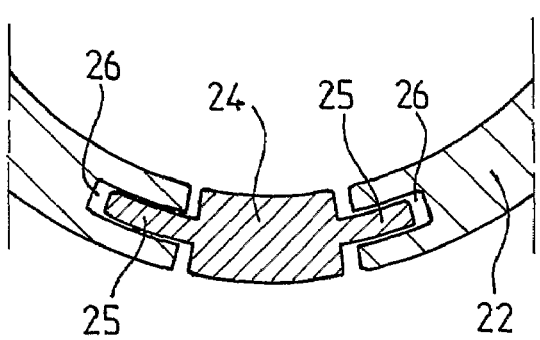
FIG. 6 is a detailed sectional view of the sheath as illustrated in the frame VI-VI.

As illustrated on FIGS. 4 to 6, the interlocking means might be formed by a lateral lug 25, capable of extending along the wall of the sleeve inside a mortice 26 arranged in said wall so as to form a baffle providing for the tightness of the sleeve to fluid. Advantageously, as illustrated on FIG. 4, as a dotted line, the lateral lug 25 is continuous on the periphery of the insert 24.

As illustrated on FIG. 6, the lug 25 of the insert 24 is capable of sliding in the mortice 26 arranged in the wall of the sleeve during the deformation of the latter while providing for the tightness.

According to an embodiment, the insert is arc-shaped by a curving radius substantially equal to the curving radius of the wall of the sleeve. The lug also shows the same curving radius. The sleeve is advantageously made of silicon flexible mouldable material. The sleeve is advantageously compound-filled in a mould where the inserts are pre-positioned.

Advantageously, the moulding operation is performed under vacuum to prevent the occurrence of inclusions, in particular bubbles.

Naturally, other embodiments, understandable to the man of the art, could have been contemplated without departing from the framework of the invention.

I claim:

1. An apparatus for measuring lateral deformation of a test piece during compression tests, the apparatus comprising:

a collar formed of a ring, said ring having a diameter suitable for clamping onto the test piece, said ring having a pair of free ends spaced by a distance from each other, said ring being formed of a metal or a composite material; and measuring means connected to said collar for measuring the distance of the space between said pair of free ends, measuring means comprising a linear variation differential transformer sensor, said sensor being slaved to one of said free ends of said ring, measuring means comprising a finger and a cam, said finger extending substantially perpendicular to a plane of said ring, said cam being slaved to the other end of said ring, said finger being cooperative with said cam.

2. The apparatus of claim 1, said cam being connected to an end of a positioning rod, said cam having a cone-shaped portion having a top surface thereof bearing against an end of said finger.

3. The apparatus of claim 1, said cam being removably connected to said positioning rod.

4. An apparatus for measuring lateral deformation of a test piece during compression tests, the apparatus comprising:

a collar formed of a ring, said ring having a diameter suitable for clamping onto the test piece, said ring having a pair of free ends spaced by a distance from each other, said ring being formed of a metal or a composite material;

measuring means connected to said collar for measuring the distance of the space between said pair of free ends, measuring means comprising a linear variation differential transformer sensor, said sensor being slaved to one of said free ends of said ring, at least one of said pair of free ends of said ring having a through bore extending perpendicular to a plane of said ring, said through bore receiving said sensor therein, the free end of said ring having an orthogonal bore tapered therein, said orthogonal bore opening at said through bore;

a locking screw cooperatively received in said orthogonal bore.

5. The apparatus of claim 4, further comprising: a guiding rod traversing both of said pair of free ends of said ring.

6. The apparatus of claim 4, measuring means comprising a finger and a cam, said cam having an angled slope, said finger bearing on said angled slope of said cam.

7. An apparatus comprising:

a sheath formed of an elastic sleeve, said sleeve having at least two hard spots evenly spaced around a circumference of said sleeve, each of the hard spots being formed by an insert, said insert having a thickness substantially equal to a thickness of a wall of said sleeve, said insert being flush with surfaces of said wall of said sleeve;

an interlocking means connected to said insert for retaining the insert in said sleeve;

a collar formed of a ring, said ring having a diameter suitable for clamping onto the test piece, said ring having a pair of free ends spaced by a distance from each other, said ring being formed of a metal or a composite material; and measuring means connected to said collar for measuring the distance of the space between said pair of free ends, measuring means comprising a linear variation differential transformer sensor, said sensor being slaved to one of said free ends of said ring, said sleeve received in said collar such that the hard spots form resting points against said collar, said sheath suitable for receiving a test piece of a mineral material therein.

8. The apparatus of claim 7, said interlocking means comprising:

lateral lug extending along a wall of said sleeve inside a mortise formed in said wall.

9. The apparatus of claim 7, said insert being arc-shaped, said insert having a radius substantially equal to a radius of the wall of said sleeve.

* * * * *